United States Patent [19]

Harrison et al.

[11] Patent Number: 5,498,539
[45] Date of Patent: Mar. 12, 1996

[54] BOVINE ENDOTHELIAL NITRIC OXIDE SYNTHASE NUCLEIC ACIDS

[75] Inventors: David G. Harrison; R. Wayne Alexander; Murphy T. J., all of Atlanta; Ken'ichi Nishida, Chamblee, all of Ga.

[73] Assignee: Daiichi Pharmaceutical Co., Ltd., Tokyo, Japan

[21] Appl. No.: 908,245

[22] Filed: Jul. 2, 1992

[51] Int. Cl.$^6$ .............................. C12N 5/10; C12N 1/21; C07H 21/04
[52] U.S. Cl. .................................. 435/240.2; 435/252.3; 435/254.2; 435/320.1; 536/23.2; 536/23.5; 536/24.31
[58] Field of Search .................. 435/195, 172.1, 435/320.1, 240.2, 252.3, 254.2; 514/44; 536/23.2, 24.31, 23.5

[56] References Cited

FOREIGN PATENT DOCUMENTS

WO/93/18156  9/1993  WIPO.

OTHER PUBLICATIONS

Sessa et al., *J. Biol. Chem.* 267(22),15274–15276 (1992).
Lamas et al., "Endothelial Nitric Oxide Synthase: Molecular cloning and Characterization of a distinct constitutive enzyme Isoform", *Proc. Natl. Acad. Sci.* 89:6348–6352 (Jul. 1992).
Pollock et al., "Purification and Characterization of Particulate Endothelium Derived Relaxing Factor Synthase From Cultured and Native Bovine Aortic Endothelial Cells", *Proc. Natl. Acad. Sci.* 88:10480–10484 (1 Dec. 1991).
Radomski et al., "The Antiaggregating Properties of Vascular Endothelium:Interactions Between Prostacyclin and Nitric Oxide", *Brit. J. Pharmacol.* 92:639–646 (Nov. 1987).
Marsden et al., "Nitric Oxide and Endothelins: Novel Autocrine/Paracrine Regulators of the Circulation", *Seminars in Nephrology* 11:169–185 (Mar. 1991).
Vane et al., "Regulatory Functions of the Vascular Endothelium:" *New England J. Med.* 323:27–36 (5 Jul. 1990).
Askew, et al., "Molecular Recognition with Convergent Functional Groups. Synthetic and Structural Studies with a Model Receptor for Nucleic Acid Components," *J. Am. Chem. Soc.* 111, 1082–1090 (1989).
Bradford, "A Rapid and Sensitive Method for the Quantitation of Microgram Quantities of Protein Utilizing the Principle of Protein–Dye Binding," *Anal. Biochem.* 72:248–254 (1976).
Bredt and Snyder, "Isolation of Nitric Oxide Synthetase, a Calmodulin–Requiring Enzyme," *Proc. Natl. Acad. Sci.* 87:682–685 (1990).
Bredt, et al., "Cloned and Expressed Nitric Oxide Synthase Structurally Resembles Cytochrome P–450 Reductase," *Nature* 351:714–718 (1991).
Forstermann, et al., "Calmodulin–Dependent Endothelium–Derived Relaxing Factor/Nitric Oxide Synthase Activity is Present in the Partriculate and Cytosolic Fractions of Bovine Aortic Endothelial Cells," *Proc. Natl. Acad. Sci.* 88:1788–1792 (1991).

Graham and VanDer, "A New Technique for the Assay of Infectivity of Human Adenovirus 5 DNA," *Virology* 52, 456 (1973).
Hibbs, et al., "Macrophage Cytotoxity: Role for L–Arginine Deiminase and Imino Nitrogen Oxidation to Nitrate," *Science* 235:473 (1987).
Kimura et al., "Isolation and Characterization of Temperature–Sensitive Mutants of Simian Virus 40" *Virology* 49, 394(1972).
Knowles, et al., "Differential Induction of Brain, Lung and Liver Nitric Oxide Synthase by Endotoxin in the Rat," *Biochem. J.* 270:833–836 (1990).
Levesque and Nerem, "The Elongation and Orientation of Cultured Endothelial Cells in Response to Shear Stress." *J. Biomech. Engnr.* 107:341–347 (1985).
Lewis and Dean, "Automated Site–Directed Drug Design: The Formation of Molecular Templates in Primary Structure Generation," *Proc. R. Soc. Lond.* 236, 125–140 and 141–162 (1989).
Lyons, et al., "Molecular Cloning and Functional Expression of an Inducible Nitric Oxide Synthase from a Murine Macrophage Cell Line," *J. Biol. Chem.* 267:6370–6374 (1992).
McKinlay and Rossmann, "Rational Design of Antiviral Agents." *Annu. Rev. Pharmacol. Toxiciol.* 29,111–122 (1989).
Mei, et al., "A Computational Approach to Mechanism of Self–Cleavage of Hammerhead RNA." *Proc. Natl. Acad. Sci.* 86:9727 (1989).
Mizushima and Nagata, " pEF–BOS, a Powerful Mammalian Expression Vector," *Nucleic. Acids, Res.* 18:5322 (1990).
Myers, et al., "Vasorelaxant Properties of the Endothelium–Derived Relaxing Factor More Closely Resemble S–Nitrosocysteine than Nitric Oxide," *Nature*, 345:161–163 (1990).

(List continued on next page.)

Primary Examiner—W. Gary Jones
Assistant Examiner—Kenneth R. Horlick
Attorney, Agent, or Firm—Kilpatrick & Cody

[57] ABSTRACT

The cloning, nucleotide and deduced amino acid sequences of the gene encoding endothelial nitric oxide synthase are described. The sequence contains binding domains for calcium/calmodulin, FMN, FAD and NADPH. The enzyme has a molecular weight of 133,413 $M_r$. The amino terminal portion of the enzyme exhibits a proline-rich region and several sites for proline-directed phosphorylation as well as a potential substrate site for acyl transferase. DNA probes prepared from the nucleic acid sequence are useful in research and diagnostically to determine the level of nitric oxide synthase mRNA expressed by endothelial cells both in cell culture and in intact tissues. These probes are also useful for detecting genetic abnormalities. The nitric oxide synthase gene is transfected into blood vessels in vivo for enhanced synthesis of nitric oxide synthase, resulting in increased production of nitric oxide. The gene is also transfected into host cells that do not normally express the enzyme for production of endothelial nitric oxide synthase in large volumes.

8 Claims, 5 Drawing Sheets

OTHER PUBLICATIONS

Nabel, et al., "Site–Specific Gene Expression in vivo by Direct Gene Transfer into the Arterial Wall," *Science* 249:1285–1288 (1990).

Nabel, et al., "Gene Transfer into Vascular Cells," *JACC* 17:189B–194B (1991).

Nabel, "Direct Gene Transfer into the Arterial Wall," *J. Vascular Surg.* 15:931–932 (1992).

Palmer, et al., "Nitric Oxide Release Accounts for the Biological Activity of Endothelium–Derived Relaxing Factor," *Nature*, 327:524–526 (1987).

Palmer, et al., "Vascular Endothelial Cells Synthesize Nitric Oxide from L–arginine," *Nature*, 333:664–666 (1988).

Perry and Davies, "The Use of 3D Modelling Databases for Identifying Structure Activity Relationship," *OSAR* Quantitative Structure–Activity Relationships in Drug Design pp. 189–193 (Alan R. Liss, Inc. 1989).

Plautz, et al., "Introduction of Vascular Smoothing Muscle Cells Expressing Recombinant Genes in Vivo," *Circulation* 83:578–583 (1991).

Potter, "Enhancer–Dependent Expression of Human K Immunoglobulin Genes Introduced into Mouse Pre–B Lymphocytes by Electroporation." *Proc. Natl. Acad. Sci. USA* 81,7161 (1984).

Rebek, et al., "Convergent Functional Groups, 3, A Molecular Cleft Recognizes Substrates of Compelmentary Size, Shape and Funcationality." *J. Am. Chem. Soc.*, 109, 2426–2431 (1987).

Rebek, "Model Studies in Molecular Recognition." *Science* 235, 1478–14848 (1987).

Renz, et al., "A Colorimetric Method for DNA Hybridization." *Nuc. Acids Res.* 12:3435–3444 (1984).

Ripka, "Computers Picture the Perfect Drug," *New Scientist* 54–57 (Jun. 16, 1988).

Sandri–Goddin, et al., "High–Frequency Transfer of Cloned Herpes Simplex Virus Type 1 Sequences to Mammalian Cells by Protoplast Fusion," *Molec. Cell Biol.* 1, 743 (1981).

Sanger, et al., "DNA Sequencing with Chain–Terminating Inhibitors," *Proc. Natl. Acad. Sci. USA* 74, 5463–5467 (1977).

Sompayrac, et al., "Efficient Infection of Monkey Cells with DNA of Simian Virus 40," *Proc. Natl. Acad. Sci. USA* 78,7575–7578 (1981).

Towler, et al., "Amino–Terminal Processing of Proteins by N–Myristoylation." *J. Biol. Chem.* 262:1030–1036 (1986).

Wood, et al., "Vascular–Smooth Muscle–Derived Relaxing Factor (MDRF) and Its Close Similarity to Nitric Oxide," *Biochem, Biophys, Res. Commun.* 170:80–88 (1990).

Xie, et al., "Cloning and Characterization of Inducible Nitric Oxide Synthase from Mouse Macrophages," *Science* 256:225–228 (1992).

Yao, et al., "Expression of Human Factor IX in Rat Capillary Endothelial Cells: Toward Somatic Gene Therapy for Hemophilia B." *Proc. Natl. Acad. Sci. USA*, 88:8101–8105 (1991).

Yui, et al., "Calmodulin–Independent Nitric Oxide Synthase from Rat Polymorphonuclear Neutrophils."*J. Biol. Chem.* 226:3369–3371 (1991).

Meyer, et al., "Partial Purification and Characterization of a $Ca^{2+}$/Calmodulin–Dependent Endothelium–Derived Relaxing Factor–Forming Enzyme from Porcine Cerebellum," *Journal of Cardiovascular Pharmacology*, 17 (Suppl. 3):S46–S51 (1991).

Schmidt, et al., "Purification of a Soluble Isoform of Guanylyl Cyclase–Activating–Factor Synthase," *Proc. Natl. Acad. Sci. USA* vol. 88, pp. 365–369 (Jan. 1991).

Sambrook, Frisch & Maniatis, *Molecular cloning: A Laboratory Manual*, 2nd Ed. (Cold Spring Harbor Laboratory, NY 1989).

BOVINE ENDOTHELIAL NITRIC OXIDE SYNTHASE NUCLEIC ACIDS

The United States government has rights in this invention by virtue of National Institutes of Health grants HL39006, HL32717, HL48252, National Science Foundation grant BCS-9111761, and Merit Review funding from the Veterans Administration.

BACKGROUND OF THE INVENTION

The endothelial cell is the interfacing cell between the blood vessel lumen and the blood. It has numerous functions including selective vessel permeability; synthesis of prostaglandins, Factor VIII antigen, and fibronectin; metabolism of chylomicrons; and the processing of several vasoactive materials such as bradykinin, serotonin and norepinephrine. The endothelial cell also synthesizes an "endothelium-derived relaxing factor" that is essential for maintenance of normal vascular homeostasis. This endothelium-derived relaxing factor has been identified by Palmer et al., *Nature*, 327:524–526 (1987), as nitric oxide. Myers et al. *Nature* 345:161–163 (1990), have further identified the endothelium-derived relaxing factor as S-nitrocysteine, a compound closely related to nitric oxide.

Nitric oxide is synthesized from the guanidino nitrogens of L-arginine, as described by Palmer et al. *Nature* 333:664–666 (1988). Nitric oxide synthase is the enzyme responsible for the production of nitric oxide from arginine. Nitric oxide synthase has recently been identified in brain by Bredt and Snyder, *Proc. Natl. Acad. Sci.* 87:682–685 (1990); in macrophages by Hibbs et al., *Science* 235:473 (1987); in neutrophils by Yui et al., *J. Biol. Chem.* 266:3369–3371 (1991); in hepatocytes by Knowles et al. *Biochem. J.* 270:833–836 (1990); in vascular smooth muscle by Wood et al. *Biochem. Biophys. Res. Commun.* 170:80–88 (1990), and in other tissues. Nitric oxide synthesis requires tetrahydrobiopterin, flavin adenine nucleotide, and NADPH as cofactors. The brain and endothelial cell nitric oxide synthase enzymes require calcium and calmodulin while the regulatory factors required by nitric oxide synthase in the macrophage and neutrophil are less well defined. The brain and macrophage nitric oxide synthases are cytosolic in location. However, endothelial cell nitric oxide synthase is membrane bound, as described by Forstermann, et al., *Proc. Natl. Acad. Sci.* 88:1788–1792 (1991). The numerous differences between brain, macrophage, and endothelial cell nitric oxide synthase indicate that the molecular structures of these isoforms are different. Recently, Bredt et al., *Nature* 351:714–718 (1991), cloned and sequenced cDNA encoding brain nitric oxide synthase, and both Xie et al., *Science* 256:225–228 (1992), and Lyons et al., *J. Biol. Chem.* 267:6370–6374 (1992), cloned and sequenced macrophage nitric oxide synthase cDNA. Attempts to use the sequence encoding brain nitric oxide synthase as a probe for expression of the enzyme in endothelial cells have been completely unsuccessful, confirming that the nitric oxide synthase expressed by these different cells are structurally distinct.

It is therefore an object of the present invention to provide nucleic acid and amino acid sequences encoding an endothelial cell nitric oxide synthase.

It is a further object of the present invention to provide a probe for nitric oxide synthase mRNA as a diagnostic tool and for studying the function and disorders involving this enzyme.

It is a further object of the present invention to transfect the gene for endothelial cell nitric oxide synthase in vivo to increase local production of nitric oxide in a blood vessel.

SUMMARY OF THE INVENTION

The cloning, nucleotide and amino acid sequences of the gene encoding endothelial nitric oxide synthase are described.

A pEF BOS cDNA library of $5 \times 10^5$ clones was prepared from bovine aortic endothelial cells and screened with a 2.8 kb cDNA BamHI fragment of rat brain nitric oxide synthase. Clone pBOS13 was found to express nitric oxide synthase activity when transfected into COS-7 cells. Sequence analysis revealed binding domains for calcium/calmodulin, FMN, FAD and NADPH. The deduced amino acid sequence revealed a protein with a molecular weight of 133,413 $M_r$ which is 58% homologous to the rat cerebellar nitric oxide synthase and 51% homologous to the rat macrophage nitric oxide synthase. The amino terminal portion of the protein exhibits several features peculiar to the endothelial cell nitric oxide synthase. These include a proline-rich region and several sites for proline-directed phosphorylation as well as a potential substrate site for acyl transferase.

DNA probes prepared from the nucleic acid sequence are used in research and clinical diagnostics to determine the level of nitric oxide synthase mRNA expressed by endothelial cells both in cell culture and in intact tissues. These probes are also used to detect genetic abnormalities.

The nitric oxide synthase gene may be used therapeutically by transfecting the gene into blood vessels in vivo for enhanced synthesis of nitric oxide synthase, resulting in increased production of nitric oxide. The gene can also be transfected into host cells that do not normally express the enzyme for production of endothelial nitric oxide synthase in large volumes.

DETAILED DESCRIPTION OF THE INVENTION

Figure 1A:
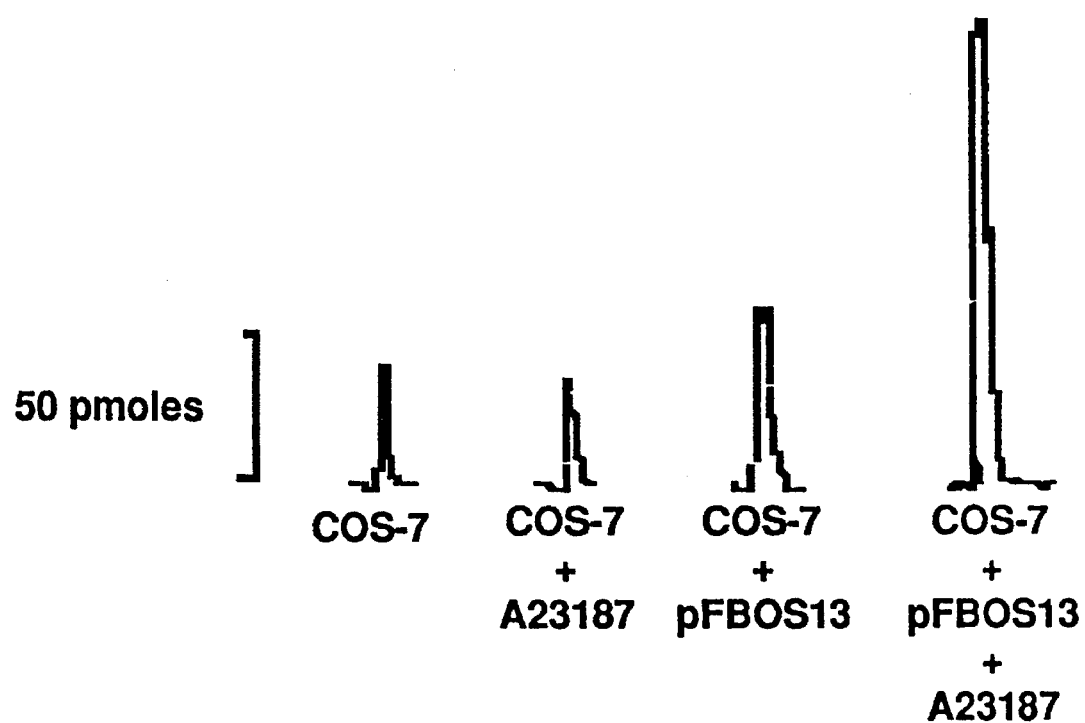
FIG. 1A is a chemiluminescence nitric oxide analyzer tracing showing the concentration, in pmoles, of nitrite produced by COS-7 cells; COS-7 cells incubated with the calcium ionophore A23187; COS-7 cells transfected with clone pFBOS-13; and COS-7 cells transfected with clone pFBOS-13 and incubated with the calcium ionophore A23187.

The gene encoding nitric oxide synthase in endothelial cells has been cloned. The cDNA nucleotide and deduced amino acid sequences are shown below:

Endothelial Cell Nitric Oxide Synthase cDNA Sequence
(Sequence Listing ID No. 1)

```
GACGGAGGCCGCCCGTCCGCCCCAGCGACATGGGCAACTTGAAGAGTGTGGGCCAGGAGCCC
GGGCCCCCCTGCGGCCTGGGGCTGGGGCTGGGCCTCGGGCTATGCGGCAAGCAGGGCCCAGC
CTCCCCGGCACCTGAGCCCAGCCGGgcCCCCGCACCCGCCACCCCGCACGCGCCAGACCACA
GCCCAGCTCCCAACAGCCCCACGCTGACCCGGCCTCCGGAGGGGCCCAAGTTCCCTCGCGTG
AAGAACTGGGAGCTGGGGAGCATCACCTACGACACTCTGTGCGCGCAGTCCCAACAGGACGG
GCCCTGCACTCCCAGGTGCTGCCTGGGCTCCCTGGTGTTGCCCCGGAAACTGCAGACCCGGC
CCTCCCCGGGACCTCCACCCGCTGAGCAGCTGCTGAGCCAGGCCAGGGACTTCATCAACCAG
TACTACAGCTCCATCAAGAGGAGCGGCTCCCAGGCTCACGAGGAGCGGCTTCAGGAGGTGGA
GGCCGAGGTGGCATCCACGGGCACCTACCACCTCCGAGAGAGCGAGCTGGTGTTCGGGGCCA
AGCAGGCCTGGCGCAACGCACCCCGCTGCGTGGGCCGCATCCAGTGGGGGAAGCTGCAGGTG
TTTGATGCCCGGGACTGCAGCTCAGCACAGGAGATGTTCACCTACATCTGCAACCACATCAA
GTACGCCACCAACCGCGGCAACCTTCGCTCGGCCATCACAGTGTTCCCGCAGCGCGCCCCGG
GCCGCGGAGACTTCCGGATCTGGAACAGCCAGCTGGTGCGCTACGCAGGCTACAGACAGCAG
GATGGCTCTGTGCGTGGGGACCCAGCCAATGTGGAGATCACGGAGCTCTGCATCCAGCACGG
CTGGACCCCCGGAAACGGCCGCTTCGACGTGCTGCCCCTGCTGCTCCAGGCCCCAGACGAGG
CTCCAGAGCTCTTTGTTCTGCCCCCCGAGCTGGTCCTTGAAGTGCCCCTGGAGCACCCCACA
CTGGAGTGGTTCGCGgCCCTGGGCCTGCGATGGTATGCCCTCCCGGCCGTGTCCAACATGCT
GCTGGAAAATCGGGGTCTGGAGTTCTCCGCGGCCCCCTTCAGCGGCTGGTACATGAGCACGG
AGATTGGCACGCGGAACCTGTGTGACCCTCACCGCTACAATATCCTGGAGGATGTGGCCGTC
TGCATGGACCTCGACACGCGGACCACCTCGTCCCTGTGGAAGGACAAGGCGGCCGTGGAGAT
CAACCTGGCTGTGCTGCACAGCTTTCAGCTCGCCAAGGTGACCATCGTGGACCACCACGCCG
CCACGGTGTCCTTCATGAAGCACCTGGACAACGAGCAGAAGGCCAGGGGGGGCTGCCCCGCC
GACTGGGCCTGGATCGTGCCCCCCATCTCAGGCAGCCTCACGCCCGTCTTCCACCAGGAGAT
GGTCAACTACATCCTGTCCCCTGCCTTCCGCTACCAGCCAGACCCCTGGAAAGGGAGCGCGA
CCAAGGGCGCAGGCATCACCAGGAAGAAGACCTTTAAGGAAGTGGCCAACGCGGTGAAGATC
TCTGCCTCACTCATGGGCACCCTGATGGCCAAGCGAGTGAAAGCAACCATCCTGTACGCCTC
TGAGACCGGCCGGGCCCAGAGCTACGCTCAGCAGCTGGGGAGGCTCTTCCGGAAGGCCTTCG
ATCCCCGGGTCCTGTGCATGGATGAGTATGACGTGGTGTCCCTGGAGCACGAGGCGCTGGTA
CTGGTGGTGACCAGCACCTTTGGGAATGGCGATCCCCGGAGAATGGAGAGAGTTTTGCAGC
TGCCCTGATGGAGATGTCGGGGCCCTACAACAGCTCCCCGCGGCCGGAACAGCACAAGAGTT
ACAAGATCCGCTTCAACAGCGTCTCCTGCTCAGACCCGCTGGTGTCCTCCTGGCGGCGGAAG
AGAaAGGAGTCCAGCAACACAGACAGTGCGGGGCCCTGGGGACCCTCAGGTTCTGTGGGTT
CGGACTGGGCTCCCGGGCATACCCCCACTTCTgCGCCTTCGCGCGAGCGGTGGACACCCGGC
TGGAAGAGCTTGGAGGGGAGCGGCTGCTGCAGCTGGGCCAGGGCGATGAGCTCTGCGGCCAG
GAAGAGGCCTTCCGTGGTTGGGCAAAGGCGGCGTTCCAGGCCTCCTGTGAGACCTTCTGCGT
TGGGGAGGAGGCCAAGGTGTGGCcCCAGGACATCTTCAGCCCCAAACGGAGCTGGAAACGCC
AGAGGTACCGGCTGAGCACCCAGGCCGAGGGGCTCCAGCTGCTGCCAGGCCTGATCCACGTG
CACAGACGGAAGATGTTTCAGGCCACAGTCCTCTCGGTGGAAAATCTGCAAAGCAGCAAGTC
CACCCGGGCCACCATCCTGGTGCGCCTGGACACTGCAGGCCAGGAGGGGCTGCAGTACCAGC
CGGGGGACCACATAGGCATCTGCCCGCCCAACCGGCCGGGCCTGGTGGAGGCCTGCTGAGC
CGCGTGGAGGACCCGCCACCGCCCACCGAGTCTGTGGCTGTGGAGCAGCTGGAGAAAGGCAG
CCCAGGCGGCCCTCCTCCCAGCTGGGTGCGGGACCCACGGCTGCCCCCGTGCACGCTGCGCC
AGGCTCTCACCTTCTTCCTGGACATCACCTCCCCACCCAGCCCCCGGCTTCTCCGACTGCTG
AGCACCCTGGCCGAAGAACCCAGCGAGCAGCAGGAGCTTGAGACCCTCAGTCAGGACCCCCG
GCGCTACGAGGAGTGGAAGTGGTTCCGCTGCCCCACGCTGCTGGAGGTGCTGGAGCAGTTCC
CGTCCGTGGCGCTGCCCGCCCGCTGCTCCTCACCCAGCTGCCCCTGCTGCAGCCCCGGTAC
TACTCTGTCAGCTCGGCCCCCAACGCCCACCCCGGAGAGGTCCACCTCACAGTGGCCGTGCT
GGCGTACAGGACCCAAGATGGGCTGGGCCCCCTACACTACGGGGTCTGCTCCACATGGCTGA
GCCAGCTCAAGACTGGAGACCCCGTGCCCTGCTTCATCAGGGGGGCTCCCTCCTTCCGGCTG
CCGCCTGACCCCTACGTGCCCTGCATCCTCGTGGGCCCTGGCACTGGCATCGCCCCCTTCCG
GGGATTTTGGCAGGAGAGGCTGCATGACATTGAGAGCAAAGGGCTGCAGCCCGCCCCCATGA
CCCTGGTGTTCGGCTGCCGCTGCTCCCAACTCGACCATCTCTACCGCGACGAGGTGCAGGAC
GCCCAGGAGCGCGGGGTGTTTGGCCGCGTCCTCACCGCCTTCTCCCGGGAACCTGACAGCCC
CAAGACCTACGTACAGGACATCCTGAGAACCGAGCTGGCTGCCGAGGTGCACCGCGTGCTGT
GCCTCGAGCGGGCCACATGTTTGTCTGCGGCGATGTCACTATGGCAACCAGCGTCCTGCAG
ACGGTGCAGCGCATCTTGGCGACAGAGGGCGACATGGAGCTGGACGAGGCGGGCGACGTCAT
CGGCGTGCTGCGGGATCAGCAACGCTATCACGAGGACATTTTCGGCCTCACGCTGCGCACCC
AGGAGGTGACAAGCCGTATACGTACCCAGAGCTTTTCCCTGCAGGAGCGGCATCTGCGGGGC
GCGGTGCCCTGGGCCTTCGACCCGCCCGGCCCAGACACCCCCGGCCCTGAAACCCCTCTTG
CTTCCCACTGCAGTTCCCGGAGAGAGGGGCTGTCATTCCACTATGGCTCTACCGCTGTCCTG
TTGGCCTTTACCGGGACCGGCCACCTCTCCCTCCCCTCCCAAGGTGACTTCCCAGAGACTGT
TGGATTCCCTGTACTATCTCATCCTCTCATCTCTAGGTCTGTTTCCCCACCCTAAGTCCATC
TGGAAGACCCCTCCCAGCAGCGGTATTCCAGAGCCTACAGTCAGCCCTTTGGTGTTTAGGTG
AATTTTAGATTCCCCTCGCCTCTCTCCGGAAGTATCTTATCTTGAAACCTGATCTCTAAATC
ATTCAAATATTTATTATTGAAGATTTACCATAAGAGACTGGACCAGAAGTTAGGAGACCTAC
TAAGATGCCTAAGCCAGTGCTGTCAATTACAGTTACAGAATAATGAAAAAAAAAAAAAAA*
```

Endothelial Cell Nitric Oxide Synthase
Deduced Amino Acid Sequence (Sequence Listing ID No. 2)

```
                                  †          †       †      †
MGNLKSVGQEPGPPCGLGLGLGLGLCGKQGPASPAPEPSRAPAPATPHAPDHSPAPNSPT

†                        †
LTRPPEGPKFPRVKNWELGSITYDTLCAQSQQDGPCTPRCCLGSLVLPRKLQTRPSPGPP

PAEQLLSQARDFINQYYSIKRSGSQAHEERQEVEAEVASTGTYHLRESELVFGAKQAW

RNAPRCVGRIQWGKLQVFDARDCSSAQEMFTYICNHIKYATNRGNLRSAITVFPQRAPGR

†
GDFRIWNSQLVRYAGYRQQDGSVRGDPANVEITELCIQHGWTPGNGRFDVLPLLLQAPDE

APELFVLPPELVLEVPLEHPTLEWFAALGLRWYALPAVSNMLLEIGGLEFSAAPFSGWYM

STEIGTRNLCDPHRYNILEDVAVCMDLDTRTTSSLWKDKAAVEINLAVLHSFQLAKVTIV

†                                 †
DHHAATVSFMKHLDNEQKARGGCPADWAWIVPPISGSLTPVFHQEMVNYILSPAFRYQPD

Ca⁺/Cam binding
PWKGSATKGAGITRKKTFKEVANAVKISASLMGTLMAKRVKATILYASETGRAQSYAQQL

GRLFRKAFDPRVLCMDEYDVVSLEHEALVLVVTSTFGNGDPPENGESFAAALMEMSGPYN
  †                                                   FMN
SSPRPEQHKSYKIRFNSVSCSDPLVSSWRRKRKESSNTDSAGALGTLRFCGFGLGSRAYP

FNM
HFCAFARAVDTRLEELGGERLLQLGQGDELCGQEEAFRGWAKAAFQASCETFCVGEEAKA

†
RPQDIFSPKRSWKRQRYRLSTQAEGLQLLPGLIHVHRRKMFQATVLSVENLQSSKSTRAT

FAD-Pyrophosphate                                        †
ILVRLDRAGQEGLQYQPGDHIGICPPNRPGLVEALLSRVEDPPPPTESVAVEQLEKGSPG

†  †
GPPPSWVRDPRLPPCTLRQALTFFLDITSPPSPRLLRLLSTLAEEPSEQQELETLSQDPR

Fad-Isoalloxanthine
RYEEWKWFRCPTLLEVLEQFPSVALPAPLLLTQLPLLQPRYYSVSSAPNAHPGEVHLTVA

NADPH—
VLAYRTQDGLGPLHYGVCSTWLSQLKTGDPVPCFIRGAPSFRLPPDPYVPCILVGPGTGI

Ribose
APFRAGFWQERLHDIESKGLQPAPMTLVFGCRCSQLDHLYRDEVQDAQERGVFGRVLTAFS
       †                 NADPH—Ribose
REPDSPKTYVQDILRTELAAEVHRVLCLERGHMFVCGDVTMATSVLQTVQRILATEGDME

LDEAGDVIGVLRDQQRYHEDIFGLTLRTQEVTSRIRTQSFSLQERHLRGAVPWAFDPPGP

†
TPGP
```

Bold residues are calcium/calmodulin, FMN, FAD, and NADPH binding domains. Underlined sequences denote potential sites of cAMP- dependent phosphorylation. The symbol † denotes potential proline-directed phosphorylation sites.

Endothelial cell nitric oxide synthase is the enzyme responsible for the production of nitric oxide from arginine and is essential for the maintenance of normal homeostasis in blood vessels. Unlike brain and macrophage nitric oxide synthase, endothelial nitric oxide synthase is membrane-bound.

The cDNA sequence of endothelial cell nitric oxide synthase, or portions thereof, are useful as probes for nitric oxide synthase mRNA in endothelial cells in vitro and in vivo, for both research and diagnostic purposes. For example, the degree of nitric oxide synthase mRNA expression in endothelial cells from blood vessels of a patient suffering from coronary disease can be analyzed with the probes, using well known hybridization techniques as described by Sambrook, Frisch & Maniatis, *Molecular Cloning: A Laboratory Manual,* 2nd Ed., (Cold Spring Harbor Laboratory, NY 1989), the teachings of which are incorporated herein by reference, to determine whether nitric oxide synthase therapy should be prescribed. If so, blood vessel endothelial cells can be transfected in vivo with a virus carrying the endothelial cell nitric oxide synthase gene to increase synthesis of the enzyme and thereby increase the production of nitric oxide within the blood vessel, or vessels, exhibiting the nitric oxide synthase deficit. Alternatively, the probes can be hybridized to DNA from a patient to detect a genetic defect in the nitric oxide synthase gene. Such defects could also be treated by transfection of blood vessel endothelial cells with the normal gene as described in more detail below.

Isolation and Sequence Determination of Nitric Oxide Synthase Gene cDNA Library Screening Poly A(+)RNA was prepared from cultured bovine aortic endothelial cells (BAEC), and cDNA was synthesized using both oligo-dT and random hexamer primers (Superscript Choice System™, BRL-Gibco, Eggenstein, Germany). Following ligation with BstXI adapters, the size fractioned cDNA was ligated into the BstXI sites of the pEF-BOS expression vector in accordance with the method described by Mizushima and Nagata, *Nucleic. Acids. Res.* 18:5322 (1990).

A $5 \times 10^5$ independent clone library was obtained after electrotransformation of E. coli DH5-alpha cells. The library was screened by colony hybridization using a 2.8 kb BamHI fragment from the rat brain nitric oxide synthase cDNA provided by Dr. David Bredt, (Johns Hopkins University, Baltimore, Md.) which was labelled with [alpha-$^{32}$P]-dCTP using the random primer method and T7 DNA polymerase. Hybridization was performed overnight on nitrocellulose membranes at 42° C. in 6 X saline sodium citrate (SSC), 5 X Denhardt's solution, 50% formamide, 0.5% sodium dodecyl sulfate (SDS), and 10 µg/ml sheared salmon sperm DNA. These were washed at 52° C. in 2 X SSC, 0.1% SDS and exposed to X-AR™ film (Kodak, Rochester, N.Y.).

Hybridizing colonies were purified by successive rounds of screening, and overlapping clones were identified by restriction enzyme analysis. The largest of these, pBOS 4.1 and pBOS-13, were 4.1 kb in length. Only pBOS 13 expressed nitric oxide synthase activity. Clone pBOS-13 was isolated from the library using a 0.9 kb SstI fragment from the 5' end of clone pBOS-4.1.

cDNA inserts were subcloned into pBluescript and nested deletions were prepared using exonuclease III. The consensus cDNA was sequenced by the dideoxy chain termination method of Sanger et al., *Proc. Natl. Acad. Sci.* USA 74:5463–5467 (1977), using a Sequenase™ kit (U.S. Biochemical Corp., Cleveland, Ohio) according to the manufacturer's instructions.

Characterization of Nitric Oxide Synthase Sequences

A 3,615 bp open reading frame begins with the first ATG at residue 30 as indicated in Sequence Listing ID No. 1. This encodes a 1,205 amino acid protein with a calculated molecular mass of 133,413 $M_r$, set forth in Sequence Listing ID No. 2. This ATG is a stronger candidate for a potential translation initiator than the next downstream ATG beginning at residue 654. The size of this deduced protein is consistent with prior estimates from studies of purified endothelial cell nitric oxide synthase. Overall, the endothelial cell nitric oxide synthase is 58% and 51% identical to the cloned rat brain and macrophage nitric oxide synthases, respectively. The carboxy-terminal two thirds of these proteins are highly homologous, while the amino terminal portions are more unique to each isozyme. Like the rat brain and macrophage nitric oxide synthases, the deduced endothelial cell nitric oxide synthase protein contains consensus binding domains for flavin adenine nucleotides (FAD), flavin mononucleotides (FMN), NADPH, and calcium/calmodulin.

The endothelial cell nitric oxide synthase has several unique features. Six potential cAMP dependent protein kinase phosphorylation sites are present at residues $Ser_{116}$, $Ser_{145}$, $Ser_{170}$, $Ser_{635}$, $Ser_{740}$ and $Ser_{1,053}$. The amino terminus of the endothelial nitric oxide synthase is rich in proline residues. This region also contains many potential phosphate acceptor sites for proline dependent protein kinase. The bovine endothelial cell nitric oxide synthase contains no strongly hydrophobic regions, suggesting an absence of membrane binding domains. In addition, $Gly_2$, followed by $Asn_3$ is one of the sequences previously identified by Towler et al., *J. Biol. Chem.* 262:1030–1036 (1986) to be a substrate for amino terminal myristoylation.

Figure 3:
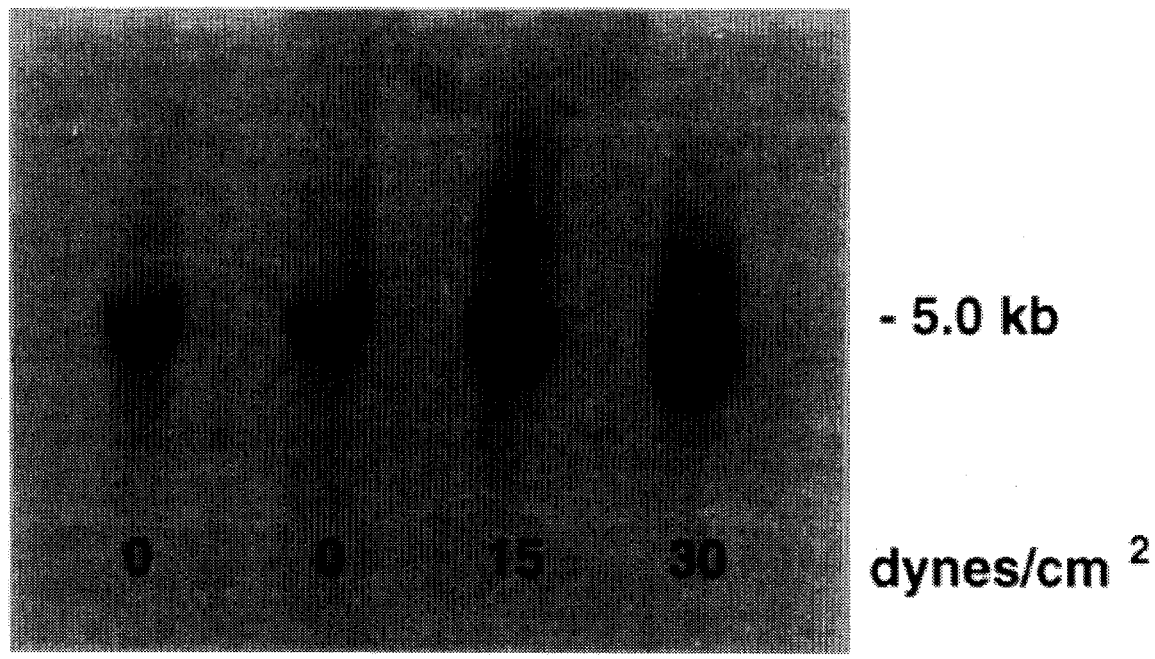
FIG. 3 is a Northern blot showing the effect of shear stress (measured in dynes/cm$^2$) on expression of nitric oxide synthase mRNA by bovine aortic endothelial cells. The 2.2 kb cDNA fragment from clone pBOS-2.2 was used as a probe.
Figure 4:
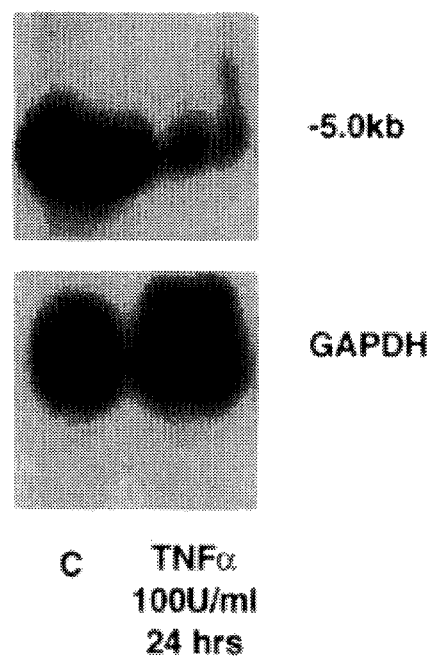
FIG. 4 is a Northern blot showing the effect of tumor necrosis factor-alpha (TNF-alpha) on nitric oxide synthase mRNA expression by bovine aortic endothelial cells. The letter "C", on the left, indicates the control showing nitric oxide synthase mRNA expression by bovine aortic endothelial cells in the absence of TNF-alpha. The blots indicating glyceraldehyde phosphate dehydrogenase (GAPDH), lower frame, were used as a control of equal loading of RNA in each lane.

Northern analysis of mRNA expression by bovine aortic endothelial cells in culture reveuled an abundant 4.8 kb message, as shown in FIGS. 3 and 4.

Endothelial Nitric Oxide Synthase Probes

As used herein, the term endothelial nitric oxide synthase sequence includes the nucleic acid sequence set forth in SEQUENCE LISTING ID No. 1, the amino acid sequence set forth in SEQUENCE LISTING ID No. 2, and functionally equivalent fragments and derivatives thereof. The sequence provided herein encoding endothelial nitric oxide synthase can be specifically used as a probe to isolate endothelial nitric oxide synthase DNA or mRNA sequences from other species, especially nitric oxide synthase mRNA from the endothelial cells of humans. Such probes can be used as diagnostic agents to detect abnormal levels of nitric oxide synthase expression in such endothelial cells. Detection of suboptimal levels of expression can be treated by gene therapy as described in more detail below.

The preferred nitric oxide synthase probe is a nucleic acid sequence that hybridizes under non-stringent hybridization conditions to the nucleic acid sequence set forth in SEQUENCE LISTING ID NO. 1. The nucleic acid sequence can be DNA or RNA. Most preferably, the probe is the nucleic acid sequence hybridizing under non-stringent hybridization conditions to the nucleic acid sequence between nucleotides 30 and 3645 of SEQUENCE LISTING ID NO. 1, or between nucleotides 700 and 2900 of SEQUENCE LISTING ID NO. 1. Non-stringent hybridization conditions are defined herein as hybridization at a temperature approximately 35° C. or more below the melting temperature of a perfectly base-paired double stranded DNA molecule. Stringent hybridization conditions are defined herein as hybridization at a temperature approximately 10° C. or more below the melting temperature of a perfectly base-paired double stranded DNA molecule. The melting temperature of a double stranded DNA molecule can be determined by methods well known to those skilled in the art.

DNA fragments can be prepared by digestion with one or more restriction enzymes. Fragments can range in size from 10 bp to 4089 bp. Alternatively, a specified polynucleotide probe can be synthesized either in a biological system or in a chemical reaction in vitro. Biological systems include both prokaryotic organisms such as bacteria and eukaryotic organisms such as yeast, isolated cells in culture, germ line cells in multicellular organisms, somatic tissue cells in multicellular organisms, or plant cells.

Preferred fragments are derived from the region of the endothelial nitric oxide synthase sequence that differs most strongly from brain and macrophage nitric oxide synthase sequences, namely the region between amino acid 1 ($Met_1$) and amino acid 120 ($Proline_{120}$). Fragments derived from this region should exhibit enhanced specificity for endothelial nitric oxide synthase and be useful as probes.

The probes may be labelled with an atom or inorganic radical most preferably using radionucleotides, such as $^{32}$P, $^3$H, $^{14}$C, $^{35}$S, $^{125}$I, or heavy metals. Preferably the label is attached to the probe by chemical conjugation. Any label may be used that provides an adequate signal and has a sufficiently long half-life. Other preferred labels include ligands, fluorescers, chemiluminescers, enzymes, antibodies and similar compounds. For example, biotin can be bound to the probe and detected by binding an avidin-conjugated enzyme or streptavidin conjugated enzyme to the biotin followed by washing to remove non-specifically bound enzyme. Upon addition of an appropriate substrate for the enzyme, the substrate is converted to a colored product that can be detected. Examples of such enzymes include alkaline phosphatase and horseradish peroxidase as described by Renz et al., *Nuc. Acids Res.* 12:3435–3444 (1984). Examples of a fluorescent labels include fluorescein and rhodamine.

The labelled nitric oxide synthase probe can be hybridized to mRNA in endothelial blood vessel cells in intact tissues or a sample containing endothelial cells obtained from a biopsy. Transcription of endothelial nitric oxide synthase mRNA can be detected by detecting the label after hybridization of the labelled probe to the sample. The method for determining the presence and quantity of a specific label depends on the label employed. Such methods are well known to those skilled in the art.

Modulatory Compounds

The sequence provided herein can also be used to screen for compounds that modulate synthesis of nitric oxide by enhancing or inhibiting transcription of the nitric oxide synthase gene. Such compounds can be identified by their ability to alter the concentration of nitric oxide synthase RNA as measured by hybridization of the RNA to a nitric oxide synthase probe. Measurement of changes in nitric oxide synthase mRNA production indirectly measures the activity of nitric oxide synthase in the endothelium. Therefore, a compound that modulates nitric oxide synthase mRNA production would most likely cause a similar increase or decrease in the production of nitric oxide synthase and could be used therapeutically to increase the levels of the enzyme in the endothelium or in research to study hemostasis.

The sequence can also be used to screen for compounds that bind directly to nitric oxide synthase permitting its localization in situ and to screen for compounds that directly or indirectly interfere with nitric oxide synthase activity. Compounds can be developed by conventional computer modelling methods as described below.

Computer Modeling

Computer modeling technology allows visualization of the three-dimensional atomic structure of a selected molecule and the rational design of new compounds that will interact with the transporter molecule. The three-dimensional construct typically depends on data from x-ray crystallographic analyses or NMR imaging of the selected molecule. The molecular dynamics require force field data. The computer graphics systems enable prediction of how a new compound will link to the target molecule and allow experimental manipulation of the structures of the compound and target molecule to perfect binding specificity. Prediction of what the molecule-compound interaction will be when small changes are made in one or both requires molecular mechanics software and computationally intensive computers, usually coupled with user-friendly, menu-driven interfaces between the molecular design program and the user.

An example of the molecular modelling system described generally above consists of the CHARMm and QUANTA programs, Polygen Corporation, Waltham, Mass. CHARMm performs the energy minimization and molecular dynamics functions. QUANTA performs the construction, graphic modelling and analysis of molecular structure. QUANTA allows interactive construction, modification, visualization, and analysis of the behavior of molecules with each other.

A number of articles review computer modeling of drugs interactive with specific proteins, such as Rotivinen, et al., *Acta Pharmaceutica Fennica* 97, 159–166 (1988); Ripka, *New Scientist* 54–57 (Jun. 16, 1988); McKinaly and Rossmann, *Annu. Rev. Pharmacol. Toxiciol.* 29, 111–122 (1989); Perry and Davies, *QSAR: Quantitative Structure-Activity Relationships in Drug Design* pp. 189–193 (Alan R. Liss, Inc. 1989); Lewis and Dean, *Proc. R. Soc. Lond.* 236, 125–140 and 141–162 (1989); and, with respect to a model receptor for nucleic acid components, Askew, et al., *J. Am. Chem. Soc.* 111, 1082–1090 (1989).

Computer modelling has found limited use in the design of compounds that will interact with nucleic acids, because the generation of force field data and x-ray crystallographic information has lagged behind computer technology. CHARMm has been used for visualization of the three-dimensional structure of parts of four RNAs, as reported by Mei, et al., *Proc. Natl. Acad. Sci.* 86:9727 (1989), but computer modelling has not been used to design compounds that will bind to and inactivate RNA.

Other computer programs that screen and graphically depict chemicals are available from companies such as BioDesign, Inc., Pasadena, Calif., Allelix, Inc, Mississauga, Ontario, Canada, and Hypercube, Inc., Cambridge, Ontario.

Synthesis of Nitric Oxide Synthase Modulating Compounds

Compounds which specifically modulate nitric oxide synthase gene transcription are synthesized using methods known to those skilled in the art based on the sequence and structure determined as described above. Known compounds can also be modified or selected on the basis of their existing structure, once the requirements for specificity are known.

The compounds can be organic, inorganic, proteins, ribozymes, or even other nucleic acids, such as antisense nucleic acids. Specific binding to the targeted molecule can be achieved by including in the molecule complementary nucleic acid sequence that forms base pairs with the synthase sequence under appropriate conditions, or by inclusion of chemical groups having the correct spatial location and charge.

In the preferred embodiments, compounds are designed as a peptide or organic compound with hydrogen bond donor and acceptor sites arranged to be complementary to the cDNA.

For peptides, the proposed hydrogen acceptors are the carbonyl oxygens of the peptide backbone; the side chains of glutamic acid, aspartic acid, asparagine, glutamine; and the imidazole nitrogen of histidine. The proposed hydrogen bond donors are the backbone amides N—H; the side chain hydroxyl groups of serine, threonine, and tyrosine; the sulfhydryl of cysteine; the indole of N—H of tryptophan; the guanidino group of arginine; the $NH_2$ of glutamine and asparagine; and the N—H of imidazole side chain of histidine.

A peptide is formed with the amino acids ordered to yield the correct spatial arrangement of hydrogen bond acceptors and donors, when the peptide is in a specific conformation induced and stabilized by binding to the target cDNA segment. The likelihood of forming the desired conformation can be refined and/or optimized using molecular computational programs.

Organic compounds can be designed to be rigid, or to present hydrogen bonding groups on edge or plane, which can interact with complementary sites. Rebek, *Science* 235, 1478–1484 (1987) and Rebek, et al., *J. Am. Chem. Soc.* 109, 2426–2431 (1987), have summarized some of these approaches and the mechanisms involved in binding of compounds to regions of proteins.

In some cases, the compound is an inhibitory compound, such as a nucleic acid molecule, and can be either RNA or DNA. This can be prepared synthetically using commercially available equipment or by cloning of an appropriate sequence which is designed or derived from the sequence to be inhibited.

The methods, reagents, and computer software programs described in the references cited herein are specifically incorporated by reference. Other methods and materials useful for molecular modeling and chemical synthesis are known to those skilled in the art.

Antibodies

Expressed protein can also be used to immunize animals to generate polyclonal antisera and/or monoclonal antibodies useful in detection and localization of nitric oxide synthase in accordance with methods well known t those skilled in the art. Because the endothelial nitric oxide synthase sequence was isolated from bovine endothelial cells, non-bovine animals should be immunized with the expressed protein to elicit an appropriate immune response.

DNA Transfection

Endothelial nitric oxide synthase DNA is transfected into cells by one of several standard published procedures to form stable transformants, including, for example, calcium phosphate precipitation, DEAE-Dextran, eletroporation, and protoplast fusion. These methods are described in detail as follows:

Calcium phosphate precipitation: DNAs are coprecipitated with calcium phosphate, according to themethod of Graham and VanDer in *Virology* 52, 456(1973), before transfer into cells. 40–50 µg of DNA with salmon sperm or calf thymus DNA as carrier is used for $0.5 \times 10^6$ cells plated on a 100 mm dish. DNA is mixed with 0.5 ml of 2X Hepes solution (280 mM NaCl, 50 mM Hepes and 1.5 mM $Na_2HPO_4$, pH 7.0) to which an equal volume of 2x $CaCl_2$ (250 mM $CaCl_2$ and 10 mM Hepes, pH 7.0) is added. A white granular precipitate appearing after 30–40 minutes is distributed dropwise evenly on the cells and allowed to sit for 4–16 hours at 37° C. The medium is removed and the cells are shocked with 15% glycerol in PBS for 3 minutes. After removing the glycerol, the cells are fed with Dulbecco's Minimal Essential Medium (DMEM) containing 10% fetal bovine serum and left in the incubator.

Protein samples are prepared for Western blot analysis by lysing cells and separating the proteins by SDS-PAGE. The proteins are transferred to nitrocellulose by electroblotting as described by Ausubek, et al., *Current Protocols in Molecular Biology* (John Wiley and Sons, 1987). After blocking the filter with instant nonfat dry milk (1 g in 100 ml PBS), primary antibody is added to the filter and incubated for 1 h at room temperature. The filter is washed thoroughly with phosphate buffered saline (PBS) and incubated with horseradish peroxidase (HRPO)-antibody conjugate for 1 hour at room temperature. The filter is again washed thoroughly with PBS and the antigen bands are identified by adding diaminobenzidine (DAB).

Enzyme assays, protein purification, and other classical biochemical methods are employed. DNA and RNA are analyzed by Southern blotting and Northern blotting techniques. Typically, the samples to be analyzed are size fractionated by gel electrophoresis. The samples, DNA or RNA, in the gels are then transferred to nitrocellulose or nylon membranes by blotting techniques. The blots, which are replicas of sample patterns in the gels, are hybridized with probes in Southern and Northern analysis. Specific bands of interest can then be visualized by detection systems such as autoradiography.

DNA can also be transferred using the DEAE-Dextran method of Kimura, et al. *Virology* 49, 394 (1972) and Sompayrac, et al., *Proc. Natl. Acad. Sci. USA* 78, 7575 (1981); the electroporation method of Potter, *Proc. Natl. Acad. Sci. USA* 81, 7161 (1984), and the protoplast fusion method of Sandri-Goddin, et al. *Molec. Cell Biol.* 1, 743 (1981).

Most preferably, the sequence encoding all or a portion of the gene for endothelial cell nitric oxide synthase is transferred into the endothelial cells of blood vessels having suboptimal levels of biologically active nitric oxide synthase by gene replacement, gene correction and gene augmentation as described generally by Nabel et al., Gene Transfer Into Vascular Cells, *JACC* 17:189B–194B (1991); and described more specifically by Nabel et al., Site-Specific Gene Expression in Vivo by Direct Gene Transfer into the Arterial Wall, *Science* 249:1285–1288 (1990); Yao et al., *Proc. Natl. Acad. Sci. USA*, 88:8101–8105 (1991); Nabel, Direct Gene Transfer into the Arterial Wall, *J. Vascular Surg.* 15:931–932 (1992) and Plautz et al., Introduction of Vascular Smooth Muscle Cells Expressing Recombinant Genes In Vivo, *Circulation*, 83:578–583 (1991), which are incorporated by reference herein.

Basically, the nitric oxide synthase gene is inserted into vascular endothelial cells by first inserting the gene sequence into a retrovirus vector, such as a murine amphotropic retroviral vector, or by infecting endothelial cells with the retrovirus containing the nitric oxide synthase gene, or by inserting the gene sequence directly into endothelial cells to create recombinant endothelial cells expressing normal or enhanced levels of nitric oxide synthase. A double balloon catheter is inserted into a blood vessel with the proximal and distal balloons of the catheter inflated, creating a protected space into which the modified retrovirus or infected or recombinant cell is introduced through an instillation port. A local region of the artery can be mechanically denuded of endothelium to allow adherence of genetically modified cells. The infected cells are instilled into the central space for 30 minutes, followed by removal of the catheter and restoration of blood flow. Polybrene™ (Sigma, St. Louis, Mo.) can be administered after installation of virus to improve the efficiency of infection. Alternatively, site-specific gene transfer is achieved by transfecting arterial segments in vivo with the use of liposomes containing a nitric oxide synthase expression vector plasmid. The gene can be coupled to a gene for a enzyme such as beta-galactoside so that successful gens transfer can be observed by analysis by X-gal staining which reveals a blue coloration in the cells that have incorporated the genes. Alternatively, nitric oxide synthase production, indicating successful transfer of the gene, can be detected with the aid of a monoclonal antibody, or nitric oxide synthase mRNA can be detected using the nitric oxide synthase probe described above.

Nitric Oxide Synthase Mutants

The nitric oxide synthase sequence can be mutated by standard procedures, such as site-directed mutagenesis or electromagnetic irradiation, and mutants screened for modified nitric oxide synthase activity, such as enzymatic activity, binding affinity and binding specificity. In this way, nitric oxide synthase having enhanced activity can be produced. For example, for isolation of a nitric oxide synthase mutant, a phosphorylated oligonucleotide primer is synthesized so that it contains a mutation in the corresponding region of the nitric oxide synthase cDNA. This first primer and a second oligonucleotide primer, without the mutation, is hybridized in solution to a single-stranded, circular plasmid construct containing a nitric oxide synthase cDNA sequence complementary to the first primer and containing vector sequences complementary to the second primer. By the addition of a DNA polymerass lacking editing activity, the oligonucleotides prime the synthesis of an extended mutant DNA sequence using the vector/nitric oxide synthase single strand as a template. Both primers are extended to where they meet and ligase is added to anneal them. This results in double-stranded particles that can be transformed into E. coli to allow for subsequent identification of mutated cDNAs through hybridizations with the mutagenic primer.

A modified nitric oxide synthase protein expressed by a mutant nitric oxide synthase gens having modified enzymatic activity can be assessed by transfecting COS cells with the mutated cDNA in an expression vector and assaying the nitric oxide synthase produced by the COS cells by a biochemical assay specific for nitric oxide synthase activity. For example, the assay can measure the amount of nitric oxide released by the cell or can measure the rate of production of nitric oxide from its precursor, L-arginine, in vitro after incubation with the mutant nitric oxide synthase. A mutation that results in a measurable increase in the concentration of nitric oxide produced or an increased rate of nitric oxide production would therefore indicate that the mutant produces nitric oxide synthase having enhanced activity. Such a mutant could be transfected into endothelial cells as described above for therapeutic use or could be used to produce large quantities of nitric oxide synthase in vitro for the subsequent production of antibodies or for scientific research.

A modified nitric oxide synthase protein having altered binding affinity or specificity for various cofactors and compounds can be isolated by mixing radiolabelled cofactor and compound in vitro with enzymatic extracts of cells that have been transfected with the mutated nitric oxide synthase sequence and detecting the amount of radioactivity or the rate of accumulation of radioactivity in the mixture. For example, a higher level of radioactivity, or an increased rate of radioactive binding indicates that the mutant has an enhanced affinity or specificity for the radioactive ligand. Such a mutant would be useful therapeutically by transfecting endothelial cells with the mutant for enhanced nitric oxide synthase activity in vivo or for increased production of nitric oxide synthase in vitro for scientific research.

The nitric oxide synthase enzyme and sequences described generally above will be further understood with reference to the following non-limiting examples.

EXAMPLE 1

Expression of Nitric Oxide Synthase in Transfected Cells Measured by Production of Nitric Oxide Expression of nitric oxide synthesis was analyzed in COS-7 cells transfected with clone pBOS-13, containing the gene for endothelial cell nitric oxide synthase.

COS-7 cells were grown to confluence in 3.5 cm plates in Dulbecco's Minimal Essential Medium and 10% fetal calf serum plus penicillin and streptomycin. At the time of transfection with clone pBOS-13, the medium was replaced with a reduced serum medium (Opti-MEM I™, BRL-Gibco, Eggenstein, Germany) and 20 µg of plasmid DNA, containing clone pBOS-13, and 50 µg lipofectin reagent (BRL, Gibco, 1 µg/ml) were added to the media for 24 hours. Nitric oxide synthase activity was measured 48 hours thereafter.

Nitric oxide synthase activity was measured by examining production of nitrite, the stable degradation product of nitric oxide, by transfected COS-7 cells. Cells were washed gently three times with a modified Krebs/HEPES buffer (composition in mM: NaCl 99.0, KCl 4.69, $CaCl_2$ 1.87, $MgSO_4$ 1.2, $NaHCO_3$ 25, $K_2HPO_4$, Na-HEPES 20, D-Glucose 11.1), and then incubated in 2 ml of the Krebs/HEPES buffer without or with 1 µM of the calcium ionophore A23187 (Sigma, St. Louis, Mo.) at 37° C. for 1 hour. In some experiments 100 µM of a nitric oxide synthase inhibitor, L—N monomethyl arginine (L—NMMA), was added to the buffer. To measure nitrite content 500 µl aliquots of the buffer from the COS-7 cells were placed in 2 ml vials and sealed with an aluminum and teflon cap. The samples were then purged of oxygen using nitrogen gas via needles inserted through the teflon. Nitrite was converted to nitric oxide gas by the addition of an excess of 5% NaI and trichloroacetic acid. The samples were then purged with a stream of nitrogen gas which was directed via vacuum into the reaction chamber of a chemiluminescence nitric oxide analyzer that was calibrated daily with nitrite standards. The results are shown in FIG. 1.

Figure 1B:
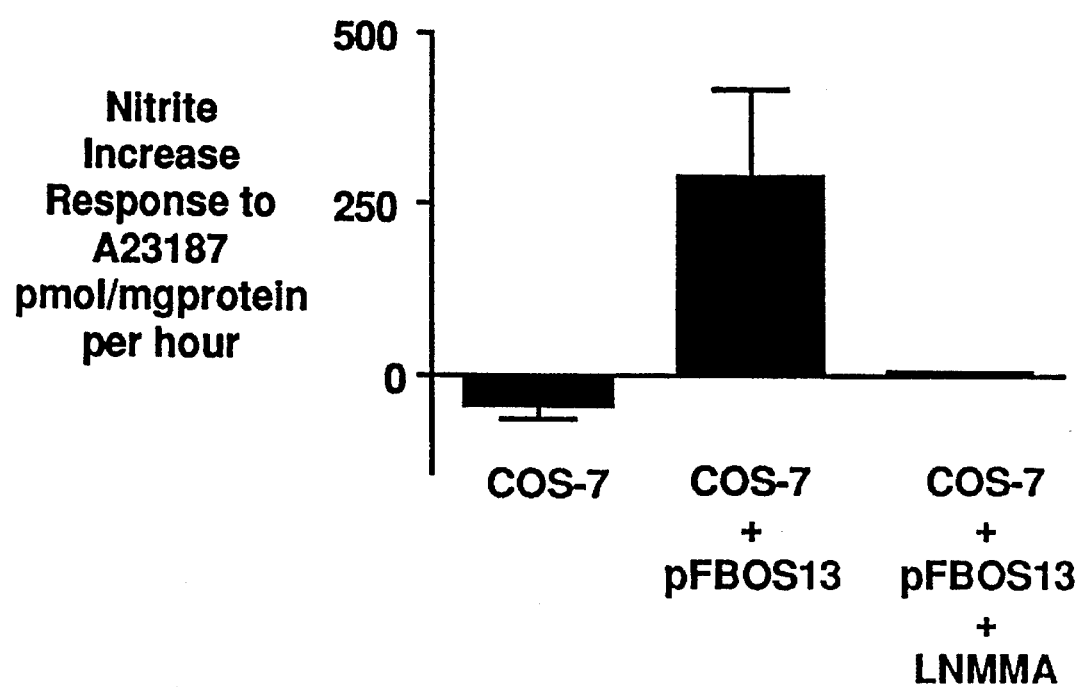
FIG. 1B is a bar graph showing the average concentration of nitrite produced, in pmol/mg protein/hour, by COS-7 cells incubated with the calcium ionophore A23187; COS-7 cells transfected with clone pFBOS-13 and incubated with the calcium ionophore A23187; and COS-7 cells transfected with pFBOS-13 and incubated with the calcium ionophore A23187 and the nitric oxide synthase inhibitor L-N-monomethyl arginine (L-NMMA).

Non-transfected COS-7 cells released small quantities of nitrite, but did not release additional nitrite in response to the calcium ionophore A23187. In contrast, COS-7 cells transfected with pBOS-13 released 287 pmoles of nitrite/hour/mg protein in response to the calcium ionophore A23187, as shown in FIGS. 1A and 1B). Nitrite release in response to the calcium ionophore A23187 was abolished in the presence of L-NMMA as shown in FIG. 1B.

EXAMPLE 2

Expression of Nitric Oxide Synthase in Transfected Cells Analysis by Western Blot A monoclonal antibody directed against the bovine aortic endothelial cell nitric oxide synthase was used to examine enzyme expression by transfected and non-transfected COS-7 cells.

Homogenates of COS-7 cells were suspended in 50 mM phosphate buffered saline containing 5 µg/ml phenylmethylsulfonylfluoride (PMSF) (Sigma, St. Louis, Mo.). Protein content was determined using a modified version of the assay described by Bradford, *Anal. Biochem.* 72:248–254 (1976). Ten µg protein was size fractionated electrophoretically using 7.5% sodium dodecyl sulfate (SDS) polyacrylamide gel. The proteins were transferred to a nitrocellulose membrane blocked with 5% casein Tris™ buffered saline solution containing 1% Tween (TBS-T™, Biorad, Rockville Centre, N.Y.), at 22° C., pH 7.6. The membranes were then incubated overnight with a 1:1000 dilution of a murine monoclonal antibody directed against the bovine aortic endothelial cell nitric oxide synthase (obtained from Jennifer Pollack and Ulrich Forstermann of Abbott Laboratories, Abbott Park, Ill.) in TBS-T™. The membranes were subsequently incubated with a goat anti-mouse secondary antibody conjugated to horseradish peroxidase (Amersham Co., Arlington Heights, Ill.). Excess antibody was removed by sequential washings with TBS-T™. Signals were detected using the enhanced chemiluminescence (ECL) detection system (Amersham Co.) on standard x-ray film.

Figure 1C:
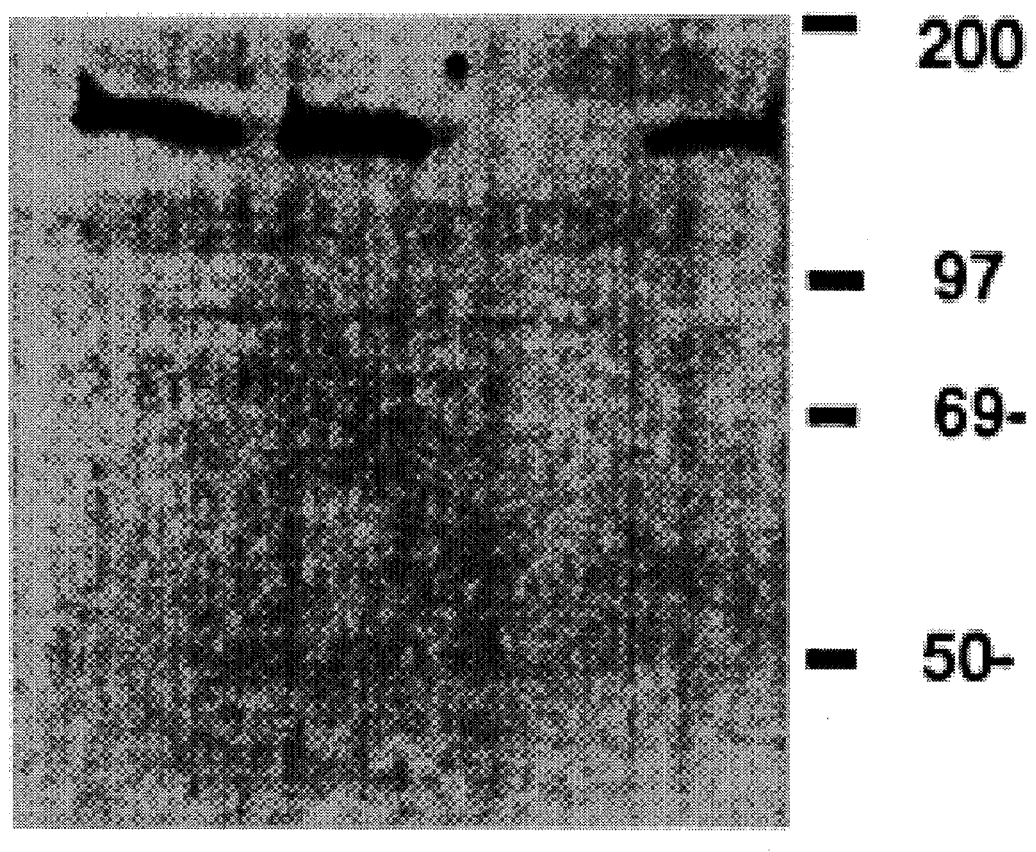
FIG. 1C is a Western immunoblot analysis of bovine aortic endothelial cell nitric oxide synthase protein content in COS-7 cells transfected with pFBOS-13 (in duplicate); untransfected COS-7 cells; and bovine aortic endothelial cells.
Figure 2:
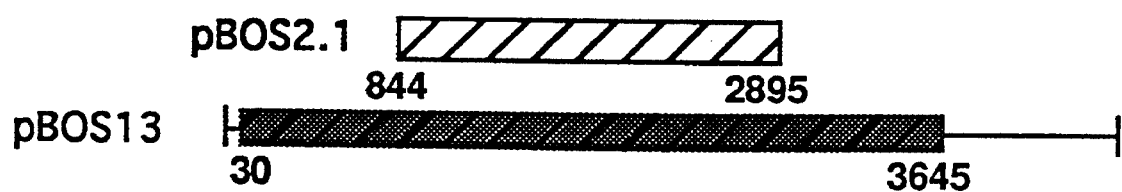
FIG. 2 is a schematic diagram of clones pBOS-13 and pBOS-2.2. The shaded area of clone pBOS-13 depicts an open reading frame.

Only COS-7 cells transfected with clone pBOS-13 expressed a protein detected by an antibody specific for purified nitric oxide synthase as shown in FIG. 1C.

EXAMPLE 3

Regulation of Nitric Oxide Synthase mRNA Expression by Sheer Stress

Elevations of chronic shear may increase endothelium-dependent vascular relaxations. To test the hypothesis that shear stress may modulate expression of nitric oxide synthase mRNA, bovine aortic endothelial cells were grown on mylar™ sheets to confluence as described by Levesque and Nerem, *J. Biomech. Engnr.* 107:341–347 (1985). Subsequently, the cells were placed in a specially designed parallel plate chamber designed to allow the application of precise quantities of steady state shear. Cells were exposed for 24 hours to either no shear, or to shear rates of 15 or 30 dynes/cm$^2$. The cells were then lysed in guanidinium isothiocanate and total RNA isolated using phenol extraction. Total RNA (20 µg) was size fractionated on a 1.0% agarose/3.0% formaldehyde gel and transferred to a nitrocellulose membrane. Hybridizations were performed overnight using a [$^{32}$P]-dCTP labelled, random primed, 2.2 kb cDNA fragment from clone pBOS 2.2. (shown schematically in FIG. 1) at 42° C., 50% formamide, 10 µg/ml sheared salmon sperm DNA in 6 X SSC, 5X Denhardt's solution and 0.5% SDS. The membranes were then washed twice for 30 minutes at 42° C., 2 X SSC, 1% SDS, and subsequently once at high stringency for 30 minutes at 65° C. using 0.2 X SSC and 0.1% SDS.

Exposure to shears of 15 and 30 dynes/cm$^2$ substantially increased nitric oxide synthase mRNA expression above that observed in cells not exposed to shear, as shown in FIG. 3.

EXAMPLE 4

Regulation of Nitric Oxide Synthase mRNA Expression by TNF-Alpha

TNF-alpha is one of the cytokines known to stimulate production of the inducible nitric oxide synthase within various tissues, including the endothelium. To determine whether this stimulation is caused by an increase in the level of transcription of mRNA from the nitric oxide synthase gene, the DNA sequence from clone pBOS-2.2 was used as a probe for nitric oxide synthase mRNA after treatment of cells with TNF-alpha.

TNF-alpha (100 U/ml, Boehringer Mannheim, Indianapolis, Ind.) was added to the medium of bovine aortic endothelial cells grown in T-75 flasks for 24 hours prior to isolation of total RNA for Northern analysis of nitric oxide synthase expression as described above in Example 2. The results are shown in FIG. 4. Glyceraldehyde phosphate dehydrogenase (GAPDH) is a gene that is not regulated, and is therefore used as an indicator of equal loading of RNA in each lane (lower frame).

In contrast to the expected effect of TNF-alpha on expression of the inducible nitric oxide synthase, the expression of mRNA identified by pBOS-2.2 was decreased by 24 hour exposure to this cytokine.

Modifications and variations of the present invention, an endothelial cell nitric oxide synthase, and the nucleic acid and amino acid sequences thereof as well as methods of use thereof, will be obvious to those skilled in the art from the foregoing detailed description. Such modifications and variations are intended to come within the scope of the appended claims.

---

We claim:

1. An isolated nucleic acid molecule having a sequence encoding bovine endothelial nitric oxide synthase wherein the sequence encodes a protein having the amino acid sequence set forth in SEQ ID NO: 2.

2. The molecule of claim 1 having the nucleic acid sequence of SEQ ID NO: 1.

3. The molecule of claim 1 further comprising a label for detection.

4. A vector comprising the molecule of claim 1 wherein said vector is suitable for expression in a host cell.

5. A host cell comprising the vector of claim 4 selected from the group consisting of procaryotic, yeast, and mammalian cells.

6. The host cell of claim 5 wherein said host cell is an endothelial cell.

7. An endothelial nitric oxide synthase probe comprising a nucleic acid having the sequence set forth in SEQ ID NO: 1 or a fragment thereof selected from the group or fragments consisting of nucleotides 30 to 3645 of SEQUENCE LISTING ID NO. 1, nucleotides 700 to 2900 of SEQUENCE LISTING ID NO. 1, and the nucleic acids corresponding to amino acids 1 to 120 of SEQ ID NO: 2.

8. The probe of claim 7 wherein the nucleic acid is labelled with a detectable marker.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 4089 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Bovine
        ( F ) TISSUE TYPE: Aorta
        ( G ) CELL TYPE: Endothelial ( x i ) SEQUENCE DESCRIPTION: SEQ ID NO:1:

```
GACGGAGGCC   GCCCGTCCGC   CCAGCGACA   TGGGCAACTT   GAAGAGTGTG   GGCCAGGAGC        60

CCGGGCCCCC   CTGCGGCCTG   GGGCTGGGGC   TGGGCCTCGG   GCTATGCGGC   AAGCAGGGCC       120

CAGCCTCCCC   GGCACCTGAG   CCCAGCCGGG   CCCCCGCACC   CGCCACCCCG   CACGCGCCAG       180
```

-continued

| | | | | | |
|---|---|---|---|---|---|
| ACCACAGCCC | AGCTCCCAAC | AGCCCCACGC | TGACCCGGCC | TCCGGAGGGG | CCCAAGTTCC | 240
| CTCGCGTGAA | GAACTGGGAG | CTGGGGAGCA | TCACCTACGA | CACTCTGTGC | GCGCAGTCCC | 300
| AACAGGACGG | GCCCTGCACT | CCCAGGTGCT | GCCTGGGCTC | CTGGTGTTG | CCCCGGAAAC | 360
| TGCAGACCCG | GCCCTCCCCG | GGACCTCCAC | CCGCTGAGCA | GCTGCTGAGC | CAGGCCAGGG | 420
| ACTTCATCAA | CCAGTACTAC | AGCTCCATCA | AGAGGAGCGG | CTCCCAGGCT | CACGAGGAGC | 480
| GGCTTCAGGA | GGTGGAGGCC | GAGGTGGCAT | CCACGGGCAC | CTACCACCTC | CGAGAGAGCG | 540
| AGCTGGTGTT | CGGGGCCAAG | CAGGCCTGGC | GCAACGCACC | CCGCTGCGTG | GGCCGCATCC | 600
| AGTGGGGGAA | GCTGCAGGTG | TTTGATGCCC | GGGACTGCAG | CTCAGCACAG | GAGATGTTCA | 660
| CCTACATCTG | CAACCACATC | AAGTACGCCA | CCAACCGCGG | CAACCTTCGC | TCGGCCATCA | 720
| CAGTGTTCCC | GCAGCGCGCC | CCGGGCCGCG | GAGACTTCCG | GATCTGGAAC | AGCCAGCTGG | 780
| TGCGCTACGC | AGGCTACAGA | CAGCAGGATG | GCTCTGTGCG | TGGGGACCCA | GCCAATGTGG | 840
| AGATCACGGA | GCTCTGCATC | CAGCACGGCT | GGACCCCCGG | AAACGGCCGC | TTCGACGTGC | 900
| TGCCCCTGCT | GCTCCAGGCC | CCAGACGAGG | CTCCAGAGCT | CTTTGTTCTG | CCCCCCGAGC | 960
| TGGTCCTTGA | AGTGCCCCTG | GAGCACCCCA | CACTGGAGTG | GTTCGCGGCC | CTGGGCCTGC | 1020
| GATGGTATGC | CCTCCCGGCC | GTGTCCAACA | TGCTGCTGGA | AATCGGGGGT | CTGGAGTTCT | 1080
| CCGCGGCCCC | CTTCAGCGGC | TGGTACATGA | GCACGGAGAT | TGGCACGCGG | AACCTGTGTG | 1140
| ACCCTCACCG | CTACAATATC | CTGGAGGATG | TGGCCGTCTG | CATGGACCTC | GACACGCGGA | 1200
| CCACCTCGTC | CCTGTGGAAG | GACAAGGCGG | CCGTGGAGAT | CAACCTGGCT | GTGCTGCACA | 1260
| GCTTTCAGCT | CGCCAAGGTG | ACCATCGTGG | ACCACCACGC | CGCCACGGTG | TCCTTCATGA | 1320
| AGCACCTGGA | CAACGAGCAG | AAGGCCAGGG | GGGGCTGCCC | CGCCGACTGG | GCCTGGATCG | 1380
| TGCCCCCCAT | CTCAGGCAGC | CTCACGCCCG | TCTTCCACCA | GGAGATGGTC | AACTACATCC | 1440
| TGTCCCCTGC | CTTCCGCTAC | CAGCCAGACC | CCTGGAAAGG | GAGCGCGACC | AAGGGCGCAG | 1500
| GCATCACCAG | GAAGAAGACC | TTTAAGGAAG | TGGCCAACGC | GGTGAAGATC | TCTGCCTCAC | 1560
| TCATGGGCAC | CCTGATGGCC | AAGCGAGTGA | AAGCAACCAT | CCTGTACGCC | TCTGAGACCG | 1620
| GCCGGGCCCA | GAGCTACGCT | CAGCAGCTGG | GGAGGCTCTT | CCGGAAGGCC | TTCGATCCCC | 1680
| GGGTCCTGTG | CATGGATGAG | TATGACGTGG | TGTCCCTGGA | GCACGAGGCG | CTGGTACTGG | 1740
| TGGTGACCAG | CACCTTTGGG | AATGGCGATC | CCCCGGAGAA | TGGAGAGAGT | TTTGCAGCTG | 1800
| CCCTGATGGA | GATGTCGGGG | CCCTACAACA | GCTCCCCGCG | GCCGGAACAG | CACAAGAGTT | 1860
| ACAAGATCCG | CTTCAACAGC | GTCTCCTGCT | CAGACCCGCT | GGTGTCCTCC | TGGCGGCGGA | 1920
| AGAGAAAGGA | GTCCAGCAAC | ACAGACAGTG | CGGGGGCCCT | GGGGACCCTC | AGGTTCTGTG | 1980
| GGTTCGGACT | GGGCTCCCGG | GCATACCCCC | ACTTCTGCGC | CTTCGCGCGA | GCGGTGGACA | 2040
| CCCGGCTGGA | AGAGCTTGGA | GGGGAGCGGC | TGCTGCAGCT | GGGCCAGGGC | GATGAGCTCT | 2100
| GCGGCCAGGA | AGAGGCCTTC | CGTGGTTGGG | CAAAGGCGGC | GTTCCAGGCC | TCCTGTGAGA | 2160
| CCTTCTGCGT | TGGGGAGGAG | GCCAAGGTGT | GGCCCCAGGA | CATCTTCAGC | CCCAAACGGA | 2220
| GCTGGAAACG | CCAGAGGTAC | CGGCTGAGCA | CCCAGGCCGA | GGGGCTCCAG | CTGCTGCCAG | 2280
| GCCTGATCCA | CGTGCACAGA | CGGAAGATGT | TCAGGCCAC | AGTCCTCTCG | GTGGAAAATC | 2340
| TGCAAAGCAG | CAAGTCCACC | CGGGCCACCA | TCCTGGTGCG | CCTGGACACT | GCAGGCCAGG | 2400
| AGGGGCTGCA | GTACCAGCCG | GGGGACCACA | TAGGCATCTG | CCCGCCCAAC | CGGCCGGGCC | 2460
| TGGTGGAGGC | GCTGCTGAGC | CGCGTGGAGG | ACCCGCCACC | GCCCACCGAG | TCTGTGGCTG | 2520
| TGGAGCAGCT | GGAGAAAGGC | AGCCCAGGCG | GCCCTCCTCC | CAGCTGGGTG | CGGGACCCAC | 2580

| | | | | | |
|---|---|---|---|---|---|
|GGCTGCCCCC|GTGCACGCTG|CGCCAGGCTC|TCACCTTCTT|CCTGGACATC|ACCTCCCCAC|2640|
|CCAGCCCCCG|GCTTCTCCGA|CTGCTCAGCA|CCCTGGCCGA|AGAACCCAGC|GAGCAGCAGG|2700|
|AGCTTGAGAC|CCTCAGTCAG|GACCCCCGGC|GCTACGAGGA|GTGGAAGTGG|TTCCGCTGCC|2760|
|CCACGCTGCT|GGAGGTGCTG|GAGCAGTTCC|CGTCCGTGGC|GCTGCCCGCC|CCGCTGCTCC|2820|
|TCACCCAGCT|GCCCCTGCTG|CAGCCCCGGT|ACTACTCTGT|CAGCTCGGCC|CCCAACGCCC|2880|
|ACCCCGGAGA|GGTCCACCTC|ACAGTGGCCG|TGCTGGCGTA|CAGGACCCAA|GATGGGCTGG|2940|
|GCCCCTACA|CTACGGGGTC|TGCTCCACAT|GGCTGAGCCA|GCTCAAGACT|GGAGACCCCG|3000|
|TGCCCTGCTT|CATCAGGGGG|GCTCCCTCCT|TCCGGCTGCC|GCCTGACCCC|TACGTGCCCT|3060|
|GCATCCTCGT|GGGCCCTGGC|ACTGGCATCG|CCCCCTTCCG|GGGATTTTGG|CAGGAGAGGC|3120|
|TGCATGACAT|TGAGAGCAAA|GGGCTGCAGC|CCGCCCCCAT|GACCCTGGTG|TTCGGCTGCC|3180|
|GCTGCTCCCA|ACTCGACCAT|CTCTACCGCG|ACGAGGTGCA|GGACGCCCAG|GAGCGCGGGG|3240|
|TGTTTGGCCG|CGTCCTCACC|GCCTTCTCCC|GGGAACCTGA|CAGCCCCAAG|ACCTACGTAC|3300|
|AGGACATCCT|GAGAACCGAG|CTGGCTGCCG|AGGTGCACCG|CGTGCTGTGC|CTCGAGCGGG|3360|
|GCCACATGTT|TGTCTGCGGC|GATGTCACTA|TGGCAACCAG|CGTCCTGCAG|ACGGTGCAGC|3420|
|GCATCTTGGC|GACAGAGGGC|GACATGGAGC|TGGACGAGGC|GGGCGACGTC|ATCGGCGTGC|3480|
|TGCGGGATCA|GCAACGCTAT|CACGAGGACA|TTTTCGGCCT|CACGCTGCGC|ACCCAGGAGG|3540|
|TGACAAGCCG|TATACGTACC|CAGAGCTTTT|CCCTGCAGGA|GCGGCATCTG|CGGGGCGCGG|3600|
|TGCCCTGGGC|CTTCGACCCG|CCCGGCCCAG|ACACCCCCGG|CCCCTGAAAC|CCCTCTTGCT|3660|
|TCCCACTGCA|GTTCCCGGAG|AGAGGGGCTG|TCATTCCACT|ATGGCTCTAC|CGCTGTCCTG|3720|
|TTGGCCTTTA|CCGGGACCGG|CCACCTCTCC|CTCCCCTCCC|AAGGTGACTT|CCCAGAGACT|3780|
|GTTGGATTCC|CTGTACTATC|TCATCCTCTC|ATCTCTAGGT|CTGTTTCCCC|ACCCTAAGTC|3840|
|CATCTGGAAG|ACCCCTCCCA|GCAGCGGTAT|TCCAGAGCCT|ACAGTCAGCC|CTTTGGTGTT|3900|
|TAGGTGAATT|TTAGATTCCC|CTCGCCTCTC|TCCGGAAGTA|TCTTATCTTG|AAACCTGATC|3960|
|TCTAAATCAT|TCAAATATTT|ATTATTGAAG|ATTTACCATA|AGAGACTGGA|CCAGAAGTTA|4020|
|GGAGACCTAC|TAAGATGCCT|AAGCCAGTGC|TGTCAATTAC|AGTTACAGAA|TAATGAAAAA|4080|
|AAAAAAAA| | | | | |4089|

( 2 ) INFORMATION FOR SEQ ID NO:2:

( i ) SEQUENCE CHARACTERISTICS:
        ( A ) LENGTH: 1205 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( v i ) ORIGINAL SOURCE:
        ( A ) ORGANISM: Bovine
        ( F ) TISSUE TYPE: Aorta
        ( G ) CELL TYPE: Endothelial ( i x ) FEATURE:
        ( A ) NAME/KEY: Binding-site
        ( B ) LOCATION: 496..512
        ( D ) OTHER INFORMATION: /note="CA++/CAM binding domain"

( i x ) FEATURE:
    ( A ) NAME/KEY: Binding-site
    ( B ) LOCATION: 651..678
    ( D ) OTHER INFORMATION: /note="FMN binding domain"

( i x ) FEATURE:
    ( A ) NAME/KEY: Binding-site
    ( B ) LOCATION: 795..806
    ( D ) OTHER INFORMATION: /note="FAD-Pyrophosphate binding
        domain"

( i x ) FEATURE:
    ( A ) NAME/KEY: Binding-site
    ( B ) LOCATION: 937..947
    ( D ) OTHER INFORMATION: /note="FAD-Isolalloxanthine
        binding domain"

( i x ) FEATURE:
    ( A ) NAME/KEY: Binding-site
    ( B ) LOCATION: 1012..1030
    ( D ) OTHER INFORMATION: /note="NADPH-Ribose binding
        domain"

( i x ) FEATURE:
    ( A ) NAME/KEY: Binding-site
    ( B ) LOCATION: 1111..1124
    ( D ) OTHER INFORMATION: /note="NADPH-Ribose binding
        domain"

( i x ) FEATURE:
    ( A ) NAME/KEY: Domain
    ( B ) LOCATION: 33..34
    ( D ) OTHER INFORMATION: /note="Potential proline directed
        phosphorylation site"

( i x ) FEATURE:
    ( A ) NAME/KEY: Domain
    ( B ) LOCATION: 46..47
    ( D ) OTHER INFORMATION: /note="Potential proline directed
        phosphorylation site"

( i x ) FEATURE:
    ( A ) NAME/KEY: Domain
    ( B ) LOCATION: 53..54
    ( D ) OTHER INFORMATION: /note="Potential proline directed
        phosphorylation site"

( i x ) FEATURE:
    ( A ) NAME/KEY: Domain
    ( B ) LOCATION: 58..59
    ( D ) OTHER INFORMATION: /note="Potential proline directed
        phosphorylation site"

( i x ) FEATURE:
    ( A ) NAME/KEY: Domain
    ( B ) LOCATION: 97..98
    ( D ) OTHER INFORMATION: /note="Potential proline directed
        phosphorylation site"

( i x ) FEATURE:
    ( A ) NAME/KEY: Domain
    ( B ) LOCATION: 116..117
    ( D ) OTHER INFORMATION: /note="Potential proline directed
        phosphorylation site"

( i x ) FEATURE:
    ( A ) NAME/KEY: Domain
    ( B ) LOCATION: 282..283
    ( D ) OTHER INFORMATION: /note="Potential proline
        phosphorylation site"

( i x ) FEATURE:
    ( A ) NAME/KEY: Domain
    ( B ) LOCATION: 459..460
    ( D ) OTHER INFORMATION: /note="Potential proline directed
        phosphorylation site"

( i x ) FEATURE:
    ( A ) NAME/KEY: Domain
    ( B ) LOCATION: 472..473

( D ) OTHER INFORMATION: /note="Potential proline directed
phosphorylation site"

( i x ) FEATURE:
( A ) NAME/KEY: Domain
( B ) LOCATION: 602..603
( D ) OTHER INFORMATION: /note="Potential proline directed
phosphorylation site"

( i x ) FEATURE:
( A ) NAME/KEY: Domain
( B ) LOCATION: 727..728
( D ) OTHER INFORMATION: /note="Potential proline directed
phosphorylation site"

( i x ) FEATURE:
( A ) NAME/KEY: Domain
( B ) LOCATION: 838..839
( D ) OTHER INFORMATION: /note="Potential proline directed
phosphorylation site"

( i x ) FEATURE:
( A ) NAME/KEY: Domain
( B ) LOCATION: 869..870
( D ) OTHER INFORMATION: /note="Potential proline directed
phosphorylation site"

( i x ) FEATURE:
( A ) NAME/KEY: Domain
( B ) LOCATION: 872..873
( D ) OTHER INFORMATION: /note="Potential proline directed
phosphorylation site"

( i x ) FEATURE:
( A ) NAME/KEY: Domain
( B ) LOCATION: 1085..1086
( D ) OTHER INFORMATION: /note="Potential proline directed
phosphorylation site"

( i x ) FEATURE:
( A ) NAME/KEY: Domain
( B ) LOCATION: 1202..1203
( D ) OTHER INFORMATION: /note="Potential proline directed
phosphorylation site"

( i x ) FEATURE:
( A ) NAME/KEY: Domain
( B ) LOCATION: 114..116
( D ) OTHER INFORMATION: /note="cAMP dependent
phosphorylation site"

( i x ) FEATURE:
( A ) NAME/KEY: Domain
( B ) LOCATION: 141..143
( D ) OTHER INFORMATION: /note="cAMP dependent
phosphorylation site"

( i x ) FEATURE:
( A ) NAME/KEY: Domain
( B ) LOCATION: 168..170
( D ) OTHER INFORMATION: /note="cAMP dependent
phosphorylation site"

( i x ) FEATURE:
( A ) NAME/KEY: Domain
( B ) LOCATION: 633..635
( D ) OTHER INFORMATION: /note="cAMP dependent
phosphorylation site"

( i x ) FEATURE:
( A ) NAME/KEY: Domain
( B ) LOCATION: 836..838
( D ) OTHER INFORMATION: /note="cAMP dependent
phosphorylation site"

( i x ) FEATURE:
( A ) NAME/KEY: Domain
( B ) LOCATION: 1051..1053
( D ) OTHER INFORMATION: /note="cAMP dependent
phosphorylation site"

( i x ) FEATURE:
  ( A ) NAME/KEY: Domain
  ( B ) LOCATION: 738..740
  ( D ) OTHER INFORMATION: /note="cAMP dependent phosphorylation site"

( x i ) SEQUENCE DESCRIPTION: SEQ ID NO:2:

```
Met Gly Asn Leu Lys Ser Val Gly Gln Glu Pro Gly Pro Pro Cys Gly
  1               5                  10                  15

Leu Gly Leu Gly Leu Gly Leu Gly Leu Cys Gly Lys Gln Gly Pro Ala
             20                  25                  30

Ser Pro Ala Pro Glu Pro Ser Arg Ala Pro Ala Pro Ala Thr Pro His
         35                  40                  45

Ala Pro Asp His Ser Pro Ala Pro Asn Ser Pro Thr Leu Thr Arg Pro
     50                  55                  60

Pro Glu Gly Pro Lys Phe Pro Arg Val Lys Asn Trp Glu Leu Gly Ser
 65                  70                  75                  80

Ile Thr Tyr Asp Thr Leu Cys Ala Gln Ser Gln Gln Asp Gly Pro Cys
                 85                  90                  95

Thr Pro Arg Cys Cys Leu Gly Ser Leu Val Leu Pro Arg Lys Leu Gln
            100                 105                 110

Thr Arg Pro Ser Pro Gly Pro Pro Pro Ala Glu Gln Leu Leu Ser Gln
        115                 120                 125

Ala Arg Asp Phe Ile Asn Gln Tyr Tyr Ser Ser Ile Lys Arg Ser Gly
    130                 135                 140

Ser Gln Ala His Glu Glu Arg Leu Gln Glu Val Glu Ala Glu Val Ala
145                 150                 155                 160

Ser Thr Gly Thr Tyr His Leu Arg Glu Ser Glu Leu Val Phe Gly Ala
                165                 170                 175

Lys Gln Ala Trp Arg Asn Ala Pro Arg Cys Val Gly Arg Ile Gln Trp
            180                 185                 190

Gly Lys Leu Gln Val Phe Asp Ala Arg Asp Cys Ser Ser Ala Gln Glu
        195                 200                 205

Met Phe Thr Tyr Ile Cys Asn His Ile Lys Tyr Ala Thr Asn Arg Gly
    210                 215                 220

Asn Leu Arg Ser Ala Ile Thr Val Phe Pro Gln Arg Ala Pro Gly Arg
225                 230                 235                 240

Gly Asp Phe Arg Ile Trp Asn Ser Gln Leu Val Arg Tyr Ala Gly Tyr
                245                 250                 255

Arg Gln Gln Asp Gly Ser Val Arg Gly Asp Pro Ala Asn Val Glu Ile
            260                 265                 270

Thr Glu Leu Cys Ile Gln His Gly Trp Thr Pro Gly Asn Gly Arg Phe
        275                 280                 285

Asp Val Leu Pro Leu Leu Leu Gln Ala Pro Asp Glu Ala Pro Glu Leu
    290                 295                 300

Phe Val Leu Pro Pro Glu Leu Val Leu Glu Val Pro Leu Glu His Pro
305                 310                 315                 320

Thr Leu Glu Trp Phe Ala Ala Leu Gly Leu Arg Trp Tyr Ala Leu Pro
                325                 330                 335

Ala Val Ser Asn Met Leu Leu Glu Ile Gly Gly Leu Glu Phe Ser Ala
            340                 345                 350

Ala Pro Phe Ser Gly Trp Tyr Met Ser Thr Glu Ile Gly Thr Arg Asn
        355                 360                 365

Leu Cys Asp Pro His Arg Tyr Asn Ile Leu Glu Asp Val Ala Val Cys
    370                 375                 380
```

```
Met Asp Leu Asp Thr Arg Thr Thr Ser Ser Leu Trp Lys Asp Lys Ala
385                 390                 395                 400

Ala Val Glu Ile Asn Leu Ala Val Leu His Ser Phe Gln Leu Ala Lys
            405                 410                 415

Val Thr Ile Val Asp His His Ala Ala Thr Val Ser Phe Met Lys His
            420                 425                 430

Leu Asp Asn Glu Gln Lys Ala Arg Gly Gly Cys Pro Ala Asp Trp Ala
        435                 440                 445

Trp Ile Val Pro Pro Ile Ser Gly Ser Leu Thr Pro Val Phe His Gln
    450                 455                 460

Glu Met Val Asn Tyr Ile Leu Ser Pro Ala Phe Arg Tyr Gln Pro Asp
465                 470                 475                 480

Pro Trp Lys Gly Ser Ala Thr Lys Gly Ala Gly Ile Thr Arg Lys Lys
            485                 490                 495

Thr Phe Lys Glu Val Ala Asn Ala Val Lys Ile Ser Ala Ser Leu Met
            500                 505                 510

Gly Thr Leu Met Ala Lys Arg Val Lys Ala Thr Ile Leu Tyr Ala Ser
            515                 520                 525

Glu Thr Gly Arg Ala Gln Ser Tyr Ala Gln Gln Leu Gly Arg Leu Phe
530                 535                 540

Arg Lys Ala Phe Asp Pro Arg Val Leu Cys Met Asp Glu Tyr Asp Val
545                 550                 555                 560

Val Ser Leu Glu His Glu Ala Leu Val Leu Val Val Thr Ser Thr Phe
            565                 570                 575

Gly Asn Gly Asp Pro Pro Glu Asn Gly Glu Ser Phe Ala Ala Ala Leu
            580                 585                 590

Met Glu Met Ser Gly Pro Tyr Asn Ser Ser Pro Arg Pro Glu Gln His
            595                 600                 605

Lys Ser Tyr Lys Ile Arg Phe Asn Ser Val Ser Cys Ser Asp Pro Leu
610                 615                 620

Val Ser Ser Trp Arg Arg Lys Arg Lys Glu Ser Ser Asn Thr Asp Ser
625                 630                 635                 640

Ala Gly Ala Leu Gly Thr Leu Arg Phe Cys Gly Phe Gly Leu Gly Ser
            645                 650                 655

Arg Ala Tyr Pro His Phe Cys Ala Phe Ala Arg Ala Val Asp Thr Arg
            660                 665                 670

Leu Glu Glu Leu Gly Gly Glu Arg Leu Leu Gln Leu Gly Gln Gly Asp
        675                 680                 685

Glu Leu Cys Gly Gln Glu Glu Ala Phe Arg Gly Trp Ala Lys Ala Ala
    690                 695                 700

Phe Gln Ala Ser Cys Glu Thr Phe Cys Val Gly Glu Glu Ala Lys Ala
705                 710                 715                 720

Arg Pro Gln Asp Ile Phe Ser Pro Lys Arg Ser Trp Lys Arg Gln Arg
            725                 730                 735

Tyr Arg Leu Ser Thr Gln Ala Glu Gly Leu Gln Leu Leu Pro Gly Leu
            740                 745                 750

Ile His Val His Arg Arg Lys Met Phe Gln Ala Thr Val Leu Ser Val
        755                 760                 765

Glu Asn Leu Gln Ser Ser Lys Ser Thr Arg Ala Thr Ile Leu Val Arg
    770                 775                 780

Leu Asp Thr Ala Gly Gln Glu Gly Leu Gln Tyr Gln Pro Gly Asp His
785                 790                 795                 800

Ile Gly Ile Cys Pro Pro Asn Arg Pro Gly Leu Val Glu Ala Leu Leu
```

|   |   |   |   | 805 |   |   |   |   | 810 |   |   |   | 815 |   |
|---|---|---|---|---|---|---|---|---|---|---|---|---|---|---|
| Ser | Arg | Val | Glu 820 | Asp | Pro | Pro | Pro | Thr 825 | Glu | Ser | Val | Ala 830 | Val | Glu |
| Gln | Leu | Glu 835 | Lys | Gly | Ser | Pro 840 | Gly | Pro | Pro | Pro 845 | Ser | Trp | Val | Arg |
| Asp | Pro 850 | Arg | Leu | Pro | Pro | Cys 855 | Thr | Leu | Arg | Gln | Ala 860 | Leu | Thr | Phe | Phe |
| Leu 865 | Asp | Ile | Thr | Ser | Pro 870 | Pro | Ser | Pro | Arg | Leu 875 | Leu | Arg | Leu | Leu | Ser 880 |
| Thr | Leu | Ala | Glu | Glu 885 | Pro | Ser | Glu | Gln | Gln 890 | Glu | Leu | Glu | Thr | Leu 895 | Ser |
| Gln | Asp | Pro | Arg 900 | Arg | Tyr | Glu | Glu | Trp 905 | Lys | Trp | Phe | Arg | Cys 910 | Pro | Thr |
| Leu | Leu | Glu 915 | Val | Leu | Glu | Gln | Phe 920 | Pro | Ser | Val | Ala | Leu 925 | Pro | Ala | Pro |
| Leu | Leu | Leu 930 | Thr | Gln | Leu | Pro 935 | Leu | Leu | Gln | Pro | Arg 940 | Tyr | Tyr | Ser | Val |
| Ser 945 | Ser | Ala | Pro | Asn | Ala 950 | His | Pro | Gly | Glu | Val 955 | His | Leu | Thr | Val | Ala 960 |
| Val | Leu | Ala | Tyr | Arg 965 | Thr | Gln | Asp | Gly | Leu 970 | Gly | Pro | Leu | His | Tyr 975 | Gly |
| Val | Cys | Ser | Thr 980 | Trp | Leu | Ser | Gln | Leu 985 | Lys | Thr | Gly | Asp | Pro 990 | Val | Pro |
| Cys | Phe | Ile 995 | Arg | Gly | Ala | Pro | Ser 1000 | Phe | Arg | Leu | Pro | Pro 1005 | Asp | Pro | Tyr |
| Val | Pro 1010 | Cys | Ile | Leu | Val | Gly 1015 | Pro | Gly | Thr | Gly | Ile 1020 | Ala | Pro | Phe | Arg |
| Gly 1025 | Phe | Trp | Gln | Glu | Arg 1030 | Leu | His | Asp | Ile | Glu 1035 | Ser | Lys | Gly | Leu | Gln 1040 |
| Pro | Ala | Pro | Met | Thr 1045 | Leu | Val | Phe | Gly | Cys 1050 | Arg | Cys | Ser | Gln | Leu 1055 | Asp |
| His | Leu | Tyr | Arg 1060 | Asp | Glu | Val | Gln | Asp 1065 | Ala | Gln | Glu | Arg | Gly 1070 | Val | Phe |
| Gly | Arg | Val 1075 | Leu | Thr | Ala | Phe | Ser 1080 | Arg | Glu | Pro | Asp | Ser 1085 | Pro | Lys | Thr |
| Tyr | Val | Gln 1090 | Asp | Ile | Leu | Arg | Thr 1095 | Glu | Leu | Ala | Ala | Glu 1100 | Val | His | Arg |
| Val | Leu 1105 | Cys | Leu | Glu | Arg | Gly 1110 | His | Met | Phe | Val 1115 | Cys | Gly | Asp | Val | Thr 1120 |
| Met | Ala | Thr | Ser | Val 1125 | Leu | Gln | Thr | Val | Gln 1130 | Arg | Ile | Leu | Ala | Thr 1135 | Glu |
| Gly | Asp | Met | Glu 1140 | Leu | Asp | Glu | Ala | Gly 1145 | Asp | Val | Ile | Gly | Val 1150 | Leu | Arg |
| Asp | Gln | Gln | Arg 1155 | Tyr | His | Glu | Asp | Ile 1160 | Phe | Gly | Leu | Thr 1165 | Leu | Arg | Thr |
| Gln | Glu | Val 1170 | Thr | Ser | Arg | Ile 1175 | Arg | Thr | Gln | Ser | Phe 1180 | Ser | Leu | Gln | Glu |
| Arg 1185 | His | Leu | Arg | Gly | Ala 1190 | Val | Pro | Trp | Ala | Phe 1195 | Asp | Pro | Pro | Gly | Pro 1200 |
| Asp | Thr | Pro | Gly | Pro 1205 |